United States Patent [19]

Janusz

[11] Patent Number: 5,384,119
[45] Date of Patent: Jan. 24, 1995

[54] METHOD OF PREVENTING NEUTROPHIL MEDIATED CONNECTIVE TISSUE DAMAGE

[75] Inventor: Michael J. Janusz, Oregonia, Ohio

[73] Assignee: Merrell Dow Pharmaceuticals Inc., Cincinnati, Ohio

[21] Appl. No.: 146,833

[22] Filed: Oct. 29, 1993

Related U.S. Application Data

[63] Continuation of Ser. No. 105,557, Aug. 12, 1993, abandoned.

[51] Int. Cl.$^6$ ............................................. A61K 31/74
[52] U.S. Cl. .............................. 424/78.08; 514/825; 514/851
[58] Field of Search .................. 514/598, 825, 851; 424/78.08; 564/49

[56] References Cited

U.S. PATENT DOCUMENTS

| | | | |
|---|---|---|---|
| 2,833,744 | 5/1958 | Neher | 260/77.5 |
| 3,528,949 | 9/1970 | Rutledge | 260/77.5 |
| 3,993,625 | 11/1976 | Kuihara et al. | 260/47 CP |
| 4,027,038 | 5/1977 | Bernstein et al. | 514/577 |
| 4,071,524 | 1/1978 | Banitt | 546/231 |
| 4,073,768 | 2/1978 | Mark | 260/45.7 |
| 4,087,548 | 5/1978 | Lenhard et al. | 514/577 |
| 4,104,262 | 8/1978 | Schade | 528/295 |
| 4,471,110 | 9/1984 | Christell | 528/337 |
| 4,604,404 | 8/1986 | Munson et al. | 514/494 |
| 4,724,235 | 2/1988 | Shanklin, Jr. et al. | 514/212 |
| 4,736,014 | 4/1988 | Englhardt | 528/295 |
| 4,824,916 | 4/1989 | Kershner et al. | 525/420 |
| 4,895,660 | 1/1990 | Kershner et al. | 210/640 |

FOREIGN PATENT DOCUMENTS

| | | |
|---|---|---|
| 0043974 | 1/1982 | European Pat. Off. . |
| 467185 | 1/1992 | European Pat. Off. . |
| 1067212 | 4/1960 | Germany . |
| 781479 | 8/1957 | United Kingdom . |
| 907829 | 8/1957 | United Kingdom . |
| 1393557 | 5/1975 | United Kingdom . |
| 2025406 | 1/1980 | United Kingdom . |
| 9200749 | 1/1992 | WIPO . |

OTHER PUBLICATIONS

R. M. Ottenbrite, ACS Symposium Series #186, pp. 205–220 (1982) "The Antitumor and Antiviral Effects of Polycarboxylic Acid Polymers".
T. Kawasaki et al., J. Biochem 106, 401–405 (1989).
P. M. Rosoff et al., J. Med. Chem 263(36), 19535–19540 (1973).
R. Seiber et al., J. of Polymer Sci., Polymer Chem. Ed. 11(6), 1439–42 (1973).
European Chem. News, p. 17 (Jul. 30, 1990).
C&E News, p. 11 (Jul. 16, 1990).
Tyms, et al., J. Cell. Biochem. vol. SUPP. pp. 365, 383 and 282 (1993).
Sakamoto, et al., The Cancer Journal, vol. 2(1):9–13 (1988).
Folkman, et al., Science, vol. 221:719–725 (1983).
Vandenberg, et al., J. of Polymer Science vol. 27(11):3745–3757 (1989).

*Primary Examiner*—Raymond J. Henley, III
*Attorney, Agent, or Firm*—Kenneth J. Collier

[57] ABSTRACT

Oligomers of the formula

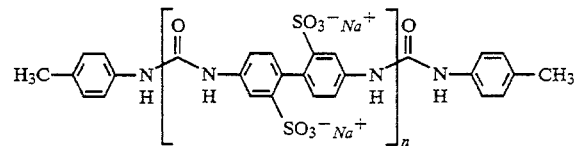

have demonstrated effectiveness in preventing connective tissue damage.

11 Claims, 8 Drawing Sheets

METHOD OF PREVENTING NEUTROPHIL MEDIATED CONNECTIVE TISSUE DAMAGE

CROSS-REFERENCE TO RELATED APPLICATION

This is a continuation of application Ser. No. 08/105,557, filed Aug. 12, 1993 now abandoned.

BACKGROUND OF THE INVENTION

The Diamino-biphenyl-disulfonic acid oligomers of the present invention are able to inhibit enzymes that are actively involved in the degradation of connective tissues. Specifically, the diamino-biphenyl-disulfonic acid oligomers of the present invention are able to inhibit the activity of elastase and cathepsin G.

Elastase and cathepsin G are serine proteases found in the primary granules of human neutrophils that have the capacity to degrade numerous connective tissue macromolecules including elastin, fibronectin, collagen and proteoglycan. Because large numbers of neutrophils are present at sites of inflammation, neutrophil elastase and cathepsin G have been implicated in the tissue destruction associated with a number of diseases including adult respiratory distress syndrome, cystic fibrosis, acute bronchitis, emphysema and arthritis.

Normally the large quantities of endogenous protease inhibitors present in plasma and mucous secretions provide ample protection against connective tissue damage mediated by neutrophil proteolytic enzymes. However, when the balance between inhibitors and proteases is disturbed tissue damage may occur. When connective tissue proteases are left unchecked the effect is a deterioration of the underlying connective tissue. This effect may result from a host of initial causes of connective tissue destruction, including direct physical injury, aging, and genetic imbalances. For instance, individuals with a genetic deficiency resulting in reduced levels of the endogenous inhibitor, α-1-antitrypsin, have a strong tendency to develop emphysema at an early age thus further supporting the enzyme imbalance theory in connective tissue diseases.

An object of this invention is the use of diaminobiphenyl-disulfonic acid oligomers as inhibitors of elastase and cathepsin G. These inhibitors thereby provides an opportunity to control disease states associated with the degradation of these tissues.

DESCRIPTION OF THE PRIOR ART

The diamino-biphenyl-disulfonic acid oligomers of this invention are described in detail in the European Patent Application published Jan. 22, 1992, under Publication No. 0467185 A2, wherein they were described as having utility in the diagnosis and/or treatment of AIDS and AIDS related complex.

The major focus of therapeutic intervention targeted at neutrophil proteolytic enzymes has centered on elastase. Free granulocyte elastase has been detected in the bronchoalavage fluids from patients with adult respiratory distress syndrome (ARDS) (McGuire, et al., *J. Clin. Invest.*, 69:543–553, 1982; Lee, et al., *N. Engl. J. Med.* 304:192–196, 1981) and in the sputum of patients with cystic fibrosis (Suter, et al, *J. Inf. Dis.* 153:902–909, 1986; Goldstein & Doting, *Am. Rev. Respir. Dis.* 134:49–56, 1986). Instillation of elastase into the lungs of hamsters induces acute damage as measured by hemorrhage (Bonney, et al., *J. Cellular Biochem.* 39:47–53, 1989. Fletcher, et al., *Am Rev. Respir. Dis,* 141:672–677, 1990, Hassall, et al., FEBS Lett. 1983:201–205, 1985) and long term changes resembling those seen in emphysema (Stone, et al., *Am. Rev. Respir. Dis* 141:47–52, 1990). The role of cathepsin G in disease states is unknown. However, elastase and cathepsin G are present in the neutrophil in approximately equal amounts and free cathepsin G has been detected along with elastase in certain pathological states. Both elastase and cathepsin G have been shown to stimulate secretion from bovine submucosal serous cells suggesting a role for these enzymes in submucosal gland hypersecretion in pulmonary disorders associated with cigarette smoking, chronic bronchitis, and cystic fibrosis (Sommerhoff, et al., *J. Clin. Invest.* 85:652–689, 1990). Recently, cathepsin G has been shown to induce platelet aggregation, calcium influx and serotonin release from platelets (Renesto et al., *Lab. Invest.* 62:409–416 1990) and to be responsible for the platelet activation stimulated by tumor necrosis factor treated neutrophils (Renesto et al., *J. Immunol.* 146:2305–2309 1991). In addition, cathepsin G has been shown to activate complement component C3 on the plasma membranes or U-937 cells (Maison et al., *J. Immunol.* 147:921–926 1991).

Previously, the degradation of cartilage matrix proteoglycan by stimulated neutrophils or neutrophil proteases was used as a model for connective tissue degradation. Using specific synthetic inhibitors of elastase or cathepsin G alone and in combination, connective tissue matrix degradation (mediated by free neutrophil proteases or breakdown occurring in the serum-antiprotease protected pericellular region between neutrophils and substrate) was found to be blocked only by inhibiting both elastase and cathepsin G (Janusz, et al., *J. Immunol.* 146:3922–3928 1991). Recently, several polyanionic polysaccharides have been shown to inhibit elastase and cathepsin G (Baici, et al., *Biochem. Pharmacol.* 29:1723–1727 1980 and Redini, et al., *Biochem. J.* 252:515–519 1988). The inhibitory capacity of these anionic polymers against the cationic elastase and cathepsin G was found to increase with polymer size and degree of sulfation.

SUMMARY OF THE INVENTION

The invention herein described discloses a method of inhibiting the activity of elastase and cathepsin G by administering a compound of the formula:

wherein n is a whole number selected from the range of 5 to 10 inclusive and the pharmaceutically acceptable salts thereof (herein also referred to as "compounds"). A preferred embodiment of the claimed compounds are those compounds wherein n is equal to 6.

An object of the invention is the use of compounds of the present invention, or the pharmaceutically acceptable salts thereof, to treat pulmonary diseases including adult respiratory distress syndrome (ARDS), chronic bronchitis, cystic fibrosis, emphysema and to treat inflammatory diseases of the joint tissues such as arthritis. These disease have in common the degradation of connective tissues.

An advantage of the present invention is that the described compounds inhibit elastase and cathepsin G, which are both known to actively contribute to, or are present during, the progression of ARDS, cystic fibrosis, acute bronchitis, emphysema, and arthritis. Specifically, the forementioned compounds have been shown to directly inhibit the human forms of elastase and cathepsin G. Because these compounds are able to inhibit human elastase and human cathepsin G, these compounds afford a mode of intervention and therapy.

Another object of the present invention is the treatment of arthritis. These compounds are advantageous by their ability to protect cartilage matrix proteoglycan (CMP) from destructive processes involving elastase and cathepsin G. Connective tissue protection of CMP by these compounds thereby affords a mode of intervention and therapy to arthritis.

Use of the compounds of the present invention may also be used to protect from acute lung injury or to protect from further damage to the lung tissues caused by elastases and cathepsin G. The present compounds can protect from connective tissue injury occurring from neutrophil elastase, and thereby, affords a means of invention and treatment of ARDS, cystic fibrosis, acute bronchitis, and emphysema.

DETAILED DESCRIPTION OF THE INVENTION

This disclosure shows that a low molecular weight sulfated polymers can block the action of elastase and cathepsin G against synthetic peptide substrates and against macromolecular connective tissue molecules. An exemplary compound within the scope of this invention was shown to inhibit elastase induced lung hemorrhage when tested in vivo. These results suggest that anionic polymers may be effective in treating neutrophil mediated connective tissue damage.

MATERIALS AND METHODS

Elastase activity is assayed using the specific substrate, N-methoxysuccinyl-Ala-Ala-Pro-Val-p-nitroanalide, and cathepsin G activity was measured using N-succinyl-Ala-Pro-Phe-p-nitroanalide. The assay buffer, 0.1M HEPES with 0.5M NaCl and 0.1% Brij-35, is used to dilute the elastase substrate to a final concentration of 0.2 mM and the cathepsin G substrate to 1 mM. The appropriate substrate in 2 ml of assay buffer is incubated at 37° C. in a heated spectrophotometer cell and the reaction is started by the addition of enzyme. In experiments where inhibitors were tested, the inhibitors were incubated with the enzyme for 5 min before the addition of substrate. Cleavage of enzyme was continuously monitored at 410 nm using a diode array spectrophotometer. Kinetic constants were determined using the kinetics software of the spectrophotometer.

Human leukocytes were isolated from citrated blood by dextran sedimentation of erythrocytes, washed free of plasma and platelets in Hank's Balanced Salt Solution (HBSS), pH 7.4, that lacked phenol red, calcium, and magnesium, and purified by gradient centrifugation. Neutrophils were collected and washed once in HBSS, incubated with distilled water for 30 seconds to lyse contaminating erythrocytes, washed twice in HBSS, resuspended in serumless media containing 10% heat inactivated fetal calf serum (FCS), glutamine (2 mM), HEPES (20 mM) and gentamycin (50 $\mu$M) and counted in a Coulter Counter. Differential staining with Diff-Quik revealed more than 95% neutrophils with 1–5% eosinophils. Viability was more than 98% as assessed by trypan blue exclusion.

Human neutrophil granule lysates were prepared by resuspending $2.5 \times 10^8$ in 4 ml of 0.34N sucrose and sonicating for 30 seconds using a microtip probe. Microscopic examination showed virtually complete breakage of the neutrophils with release of the granules. The neutrophil lysate was centrifuged at $1000 \times g$ for 10 min. at 4° C., the supernatant was collected and centrifuged at $30,000 \times g$ for 30 min. at 4° C. and the pellet containing neutrophil granules was resuspended in 2 ml of 0.05M sodium acetate buffer, pH 5.5, containing 1M NaCl and 0.1% Brij-35 and kept on ice for 30 min. with several brief sonications of approximately 30 seconds during the incubation period. Microscopic examination showed disruption of the granules. The granule lysate was centrifuged at $30,000 \times g$ for 30 min. at 4° C. and the supernatant was collected, tested for elastase and cathepsin G content using synthetic substrates as described above, aliquoted and stored at 70° C. until used.

PREPARATION OF RADIOLABELED BOVINE CARTILAGE

Fresh bovine nasal septa were obtained from a local abattoir and 4 mm cartilage cylinders were prepared using a No. 2 cork borer. The cylinders were sliced into 1 mm discs. The top and bottom discs were discarded and the remaining cartilage discs were pooled, washed three times in HBSS and resuspended in Dulbecco's Modified Eagles Medium (DMEM) with antibiotics and supplements. The sulfated sugars that constitute the glycosaminoglycan side chains of cartilage proteoglycan were radiolabeled by the addition of 10 $\mu$Ci/ml of Na$_2{}^{35}$SO$_4$ followed by incubation overnight at 37° C. with gentle rocking. The radioactive medium was removed and the discs were washed ten times with HBSS to remove unincorporated label. The radiolabeled cartilage discs were freeze-thawed five times and heated at 65° C. for 15 min. to kill chondrocytes and inactivate endogenous enzymes. This treatment eliminated autolysis of the cartilage but did not significantly alter the sensitivity of the proteoglycan to exogenous proteases. The majority of the discs used in these studies contained $5.0 \times 10^4$ to $2.0 \times 10^5$ dpm of incorporated $^{35}$S.

Neutrophil Protease Degradation Of Connective Tissue Matrix

The ability of neutrophil proteases to degrade connective tissue matrix was measured by incubating $^{35}$S-radiolabeled cartilage discs with neutrophil lysate, purified elastase or cathepsin G in serumless media for 4 hours at 37° C. and collecting the supernatants and counting the radiolabeled material in the supernatants and discs. The radioactivity remaining in the cartilage discs after removal of the supernatant was assayed by completely digesting the discs in 6M HCl at 100° C. for 1 hour, removing the HCl by vacuum evaporation and resuspending the dried material in 0.5 ml HBSS. Supernatants and processed discs were counted in a Beckman LS 3801 scintillation counter. The data were expressed as the percent at $^{35}$S label released into the supernatant.

Connective Tissue Degradation By Human Neutrophils

Radiolabeled cartilage discs were placed into the wells of 96-well microtiter plates and overlayed with human neutrophils suspended in DMEM containing 10% FCS. The neutrophils were stimulated by the addition of 1 mg/ml of opsonized zymosan and incubated for 4 hours at 37° C. with 5% CO$_2$. Connective tissue matrix degradation was quantitated by the amount of radiolabel released. In experiments using protease inhibitors, the inhibitors were added immediately after the neutrophils. The viability of the neutrophils incubated with the protease inhibitors was determined by assaying the supernatants for lactic dehydrogenase (LDH) and by neutrophil exclusion of trypan blue. In addition, the effect of protease inhibitors on primary granule enzyme secretion was monitored by measuring the release of myeloperoxidase.

Elastase Induced Pulmonary Hemorrhage

Male Sprague Dawley rats were anesthetized with chloral hydrate (300 mg/kg) and either saline or human neutrophil elastase was administered intratracheally. Briefly, rats were placed on a surgical board, ventral side up, and their mouths held open using a rubber band placed over their incisors. The tongue was held to the side and 100 micro liters of elastase solution (1 mg/ml) was administered into the trachea with the aid of a bright light source and a 3 inch, 22 gauge blunt-end needle. One hour after elastase administration, the rats were sacrificed using $CO_2$ and the trachea was surgically exposed and cannulated. The lungs were lavaged with 10 ml of saline and the hemoglobin content was determined using the cyanmethemoglobin assay. In experiments where inhibitors were tested, the compounds were given intratracheally in 100 $\mu$l of saline at various times before elastase administration.

RESULTS AND DESCRIPTION OF FIGURES 1-8

Figure 1:
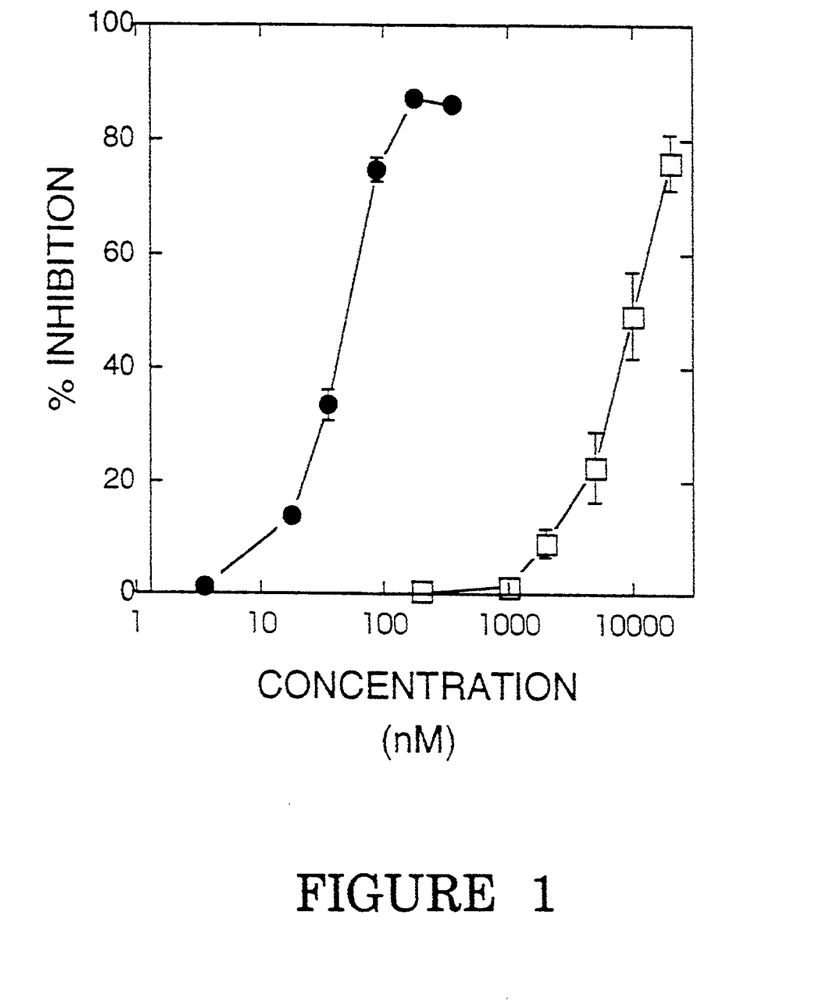
Figure 2:
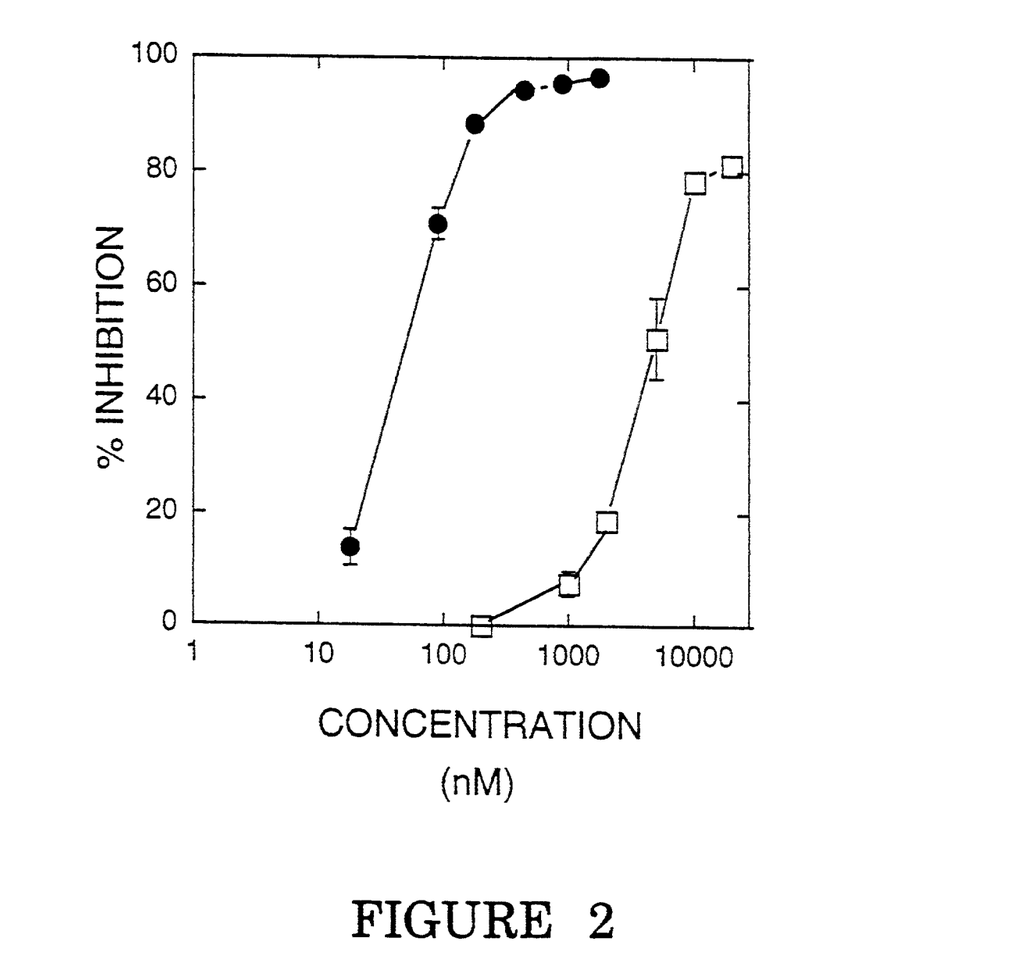

Inhibition Of Elastase And Catheosin G Cleavage Of Synthetic Substrates By Sulfated Polymers The ability of several sulfated polymers to inhibit elastase and cathepsin G degradation of their respective substrates was examined. MDL-101,028, a compound falling within the scope of the claimed invention, where the value of n is 6, and 4,4'-Diisothiocyanatostilbene-2,2'-disulfonic acid, internally identified as MDL-101,114 (DIDS) inhibited both elastase and cathepsin G in a dose-dependent manner. The $IC_{50}$ for the inhibition of 2 $\mu$g of elastase was 40 nM for MDL-101,028(•-•) and 1100 nM for DIDS (□-□) (FIG. 1). Slightly higher concentrations of compounds were required for the inhibition of 2 micrograms of cathepsin G with an $IC_{50}$ of 80 nM and 1400 nM for MDL-101,028(•-•) and DIDS (□-□) respectively (FIG. 2).

Figure 3:
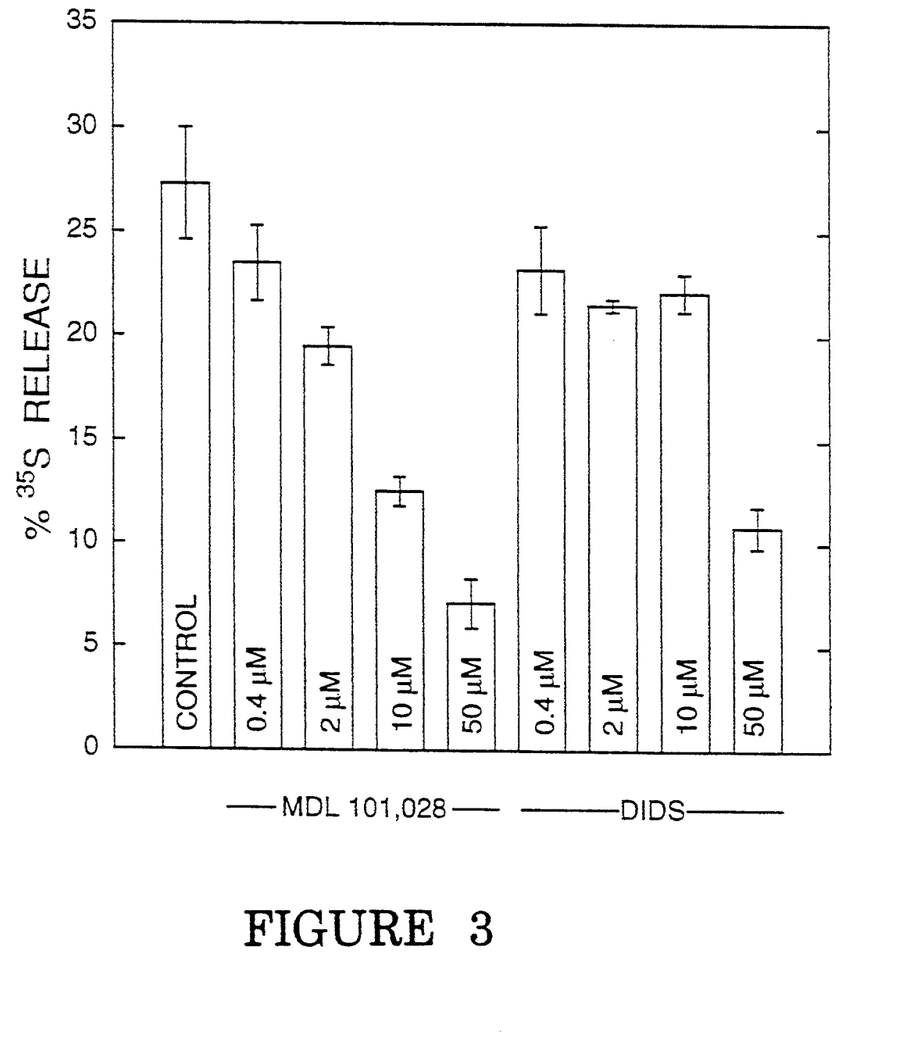
Figure 4:
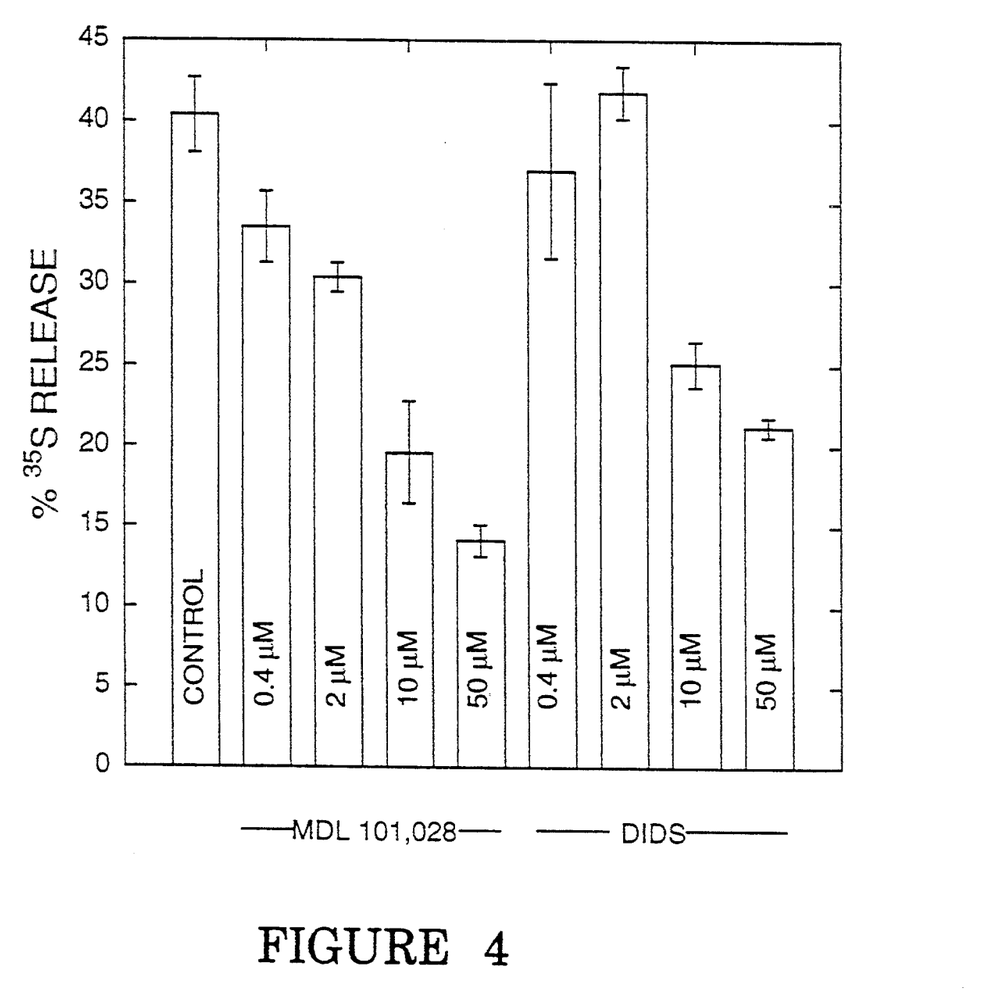

Effect Of Sulfated Polymers On Elastase And Cathepsin G Degradation Of Cartilage Matrix Proteoglycan Cartilage matrix proteoglycan (CPG) was used as a model system for the degradation of macromolecular connective tissue substrate. Both purified human neutrophil elastase and cathepsin G degrade CPG in a dose and time-dependent manner. MDL-101,028 inhibited both elastase (FIG. 3) and cathepsin G (FIG. 4) mediated CPG degradation in a dose-dependent manner with an $IC_{50}$ of approximately 8 and 9 $\mu$M, respectively. MDL 101,114 also inhibited elastase (FIG. 3) and cathepsin G (FIG. 4) mediated cartilage degradation with $IC_{50}$'s of 38 and 50 $\mu$m, respectively.

Figure 5:
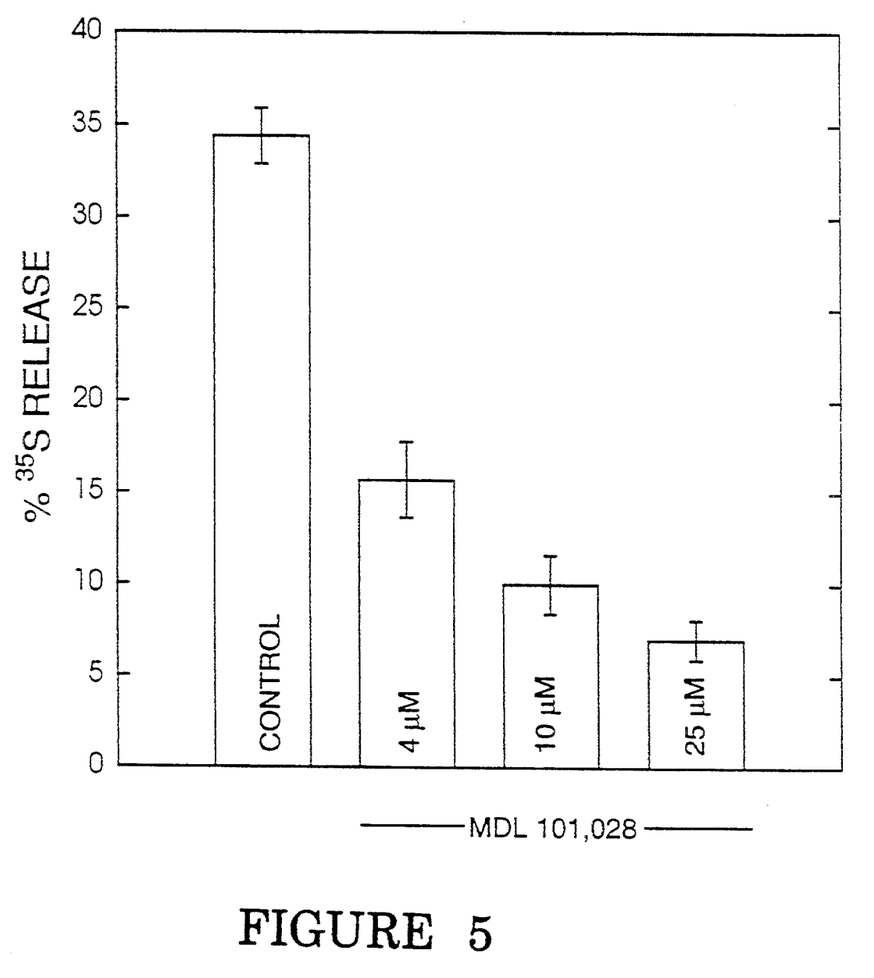

Effect Of Sulfated Polymers On Human Neutrophil Lysate Mediated Degradation Of CPG Human neutrophil lysate at a 1:100 dilution in serumless media degraded CPG by 34%±2% (mean+−S.E.M., n=3) after a 4 hour incubation at 37° C. (FIG. 5). MDL-101,028 inhibited CPG degradation by 54%, 70%, and 79%, at concentrations of 4, 10, and 25 $\mu$molar respectively (FIG. 5).

Effect Of Sulfated Polymers On CPG Degradation Mediated By Human Neutrophils

Figure 6:
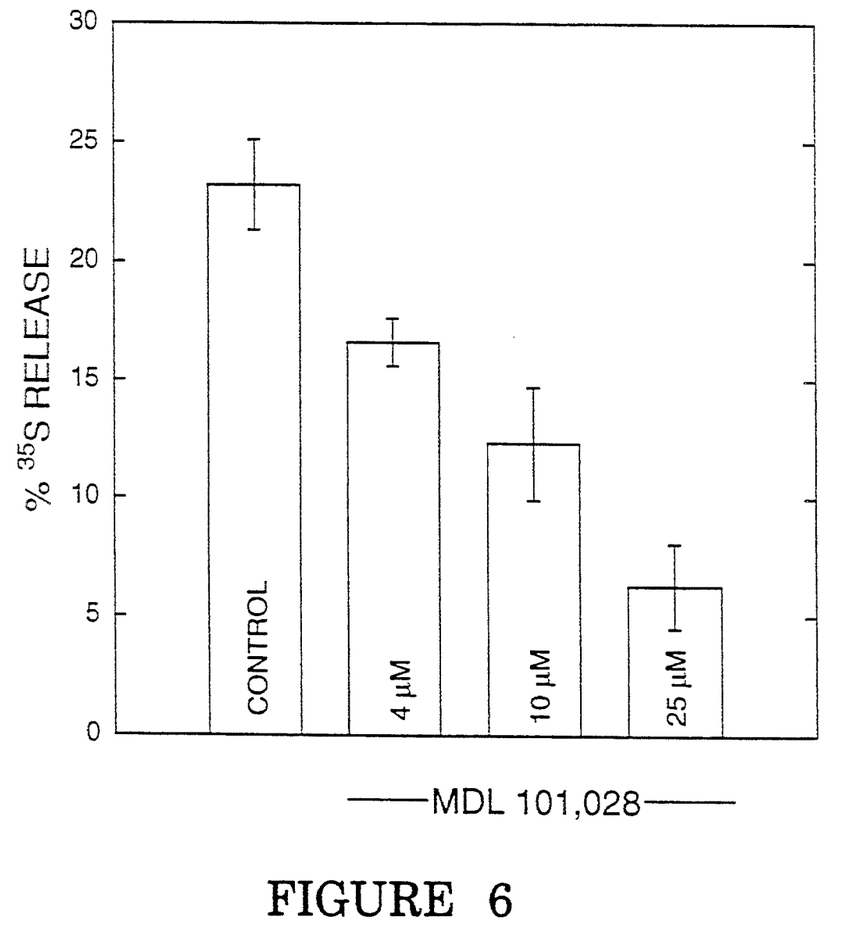

Human neutrophils in media containing 10% FCS were allowed to settle onto cartilage discs in the wells of microtiter plates and were stimulated with 1 mg/ml of opsonized zymosan and incubated at 37° C. for 4 hours in the presence and absence of sulfated polymers. Stimulated neutrophils in the presence of serum antiproteases degraded CPG by 23% plus or minus 2% (±S.E.M., n=4) (FIG. 6). Incubation of stimulated human neutrophils with MDL-101,028 inhibited CPG degradation by 31%, 47%, and 73% at concentrations of 4, 10 and 25 $\mu$molar, respectively.

The viability of the neutrophils was not diminished by treatment with MDL-101,028 as assessed by trypan blue exclusion and by lactic dehydrogenase release. The percentage of neutrophils stimulated with zymosan in media for 4 hours that excluded trypan blue was 85% compared to 77%-87% for neutrophils incubated with MDL-101,028 at doses of 4, 10, and 25 $\mu$M, respectively. This correlated with LDH release which was 9% for stimulated neutrophils treated with media, compared to 7-11% for neutrophils incubated with MDL-101,028 at concentrations of 4-25 $\mu$M. MDL-101,028 which did not inhibit CPG degradation by blocking enzyme release from neutrophils as myeloperoxidase release was not inhibited.

MDL-101,028 Inhibits Elastase Induced Lung Hemorrhage In Rats

Figure 7:
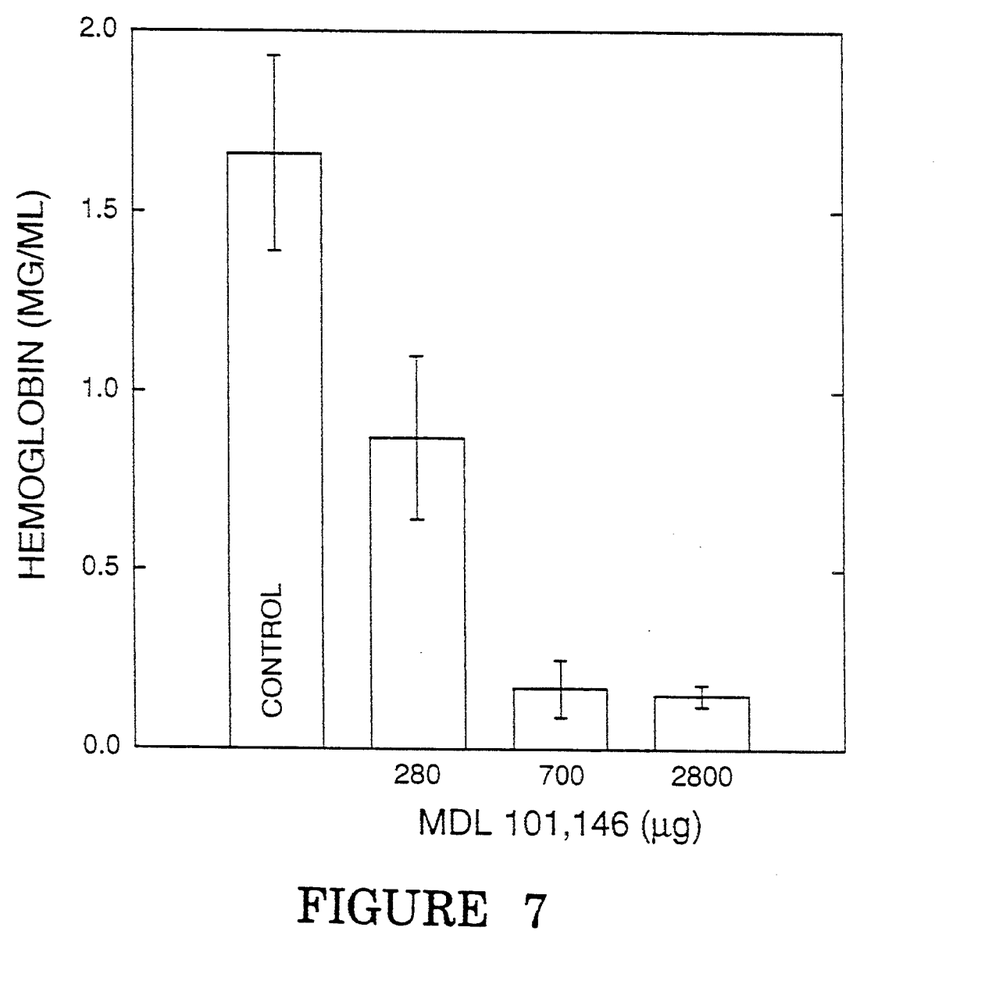

Intratracheal instillation of human leukocyte elastase produced acute lung injury as assessed by hemorrhage (FIG. 7). The hemorrhage was quantified by measuring the hemoglobin content of the pulmonary lavage fluid. Instillation of 100 $\mu$g of neutrophil elastase intratracheally into rats resulted in a bright red hemorrhagic lung lavage fluid that contained 1.7±0.3 (mean±SEM, n=12) mg/ml hemoglobin of (FIG. 7). When MDL-101,028 was administered intratracheally immediately before elastase (within 30 seconds) at doses of 280 $\mu$g, 700 $\mu$g, or 2800 $\mu$g, lung hemorrhage was inhibited by 48%, 90%, and 90% respectively (FIG. 7).

Figure 8:
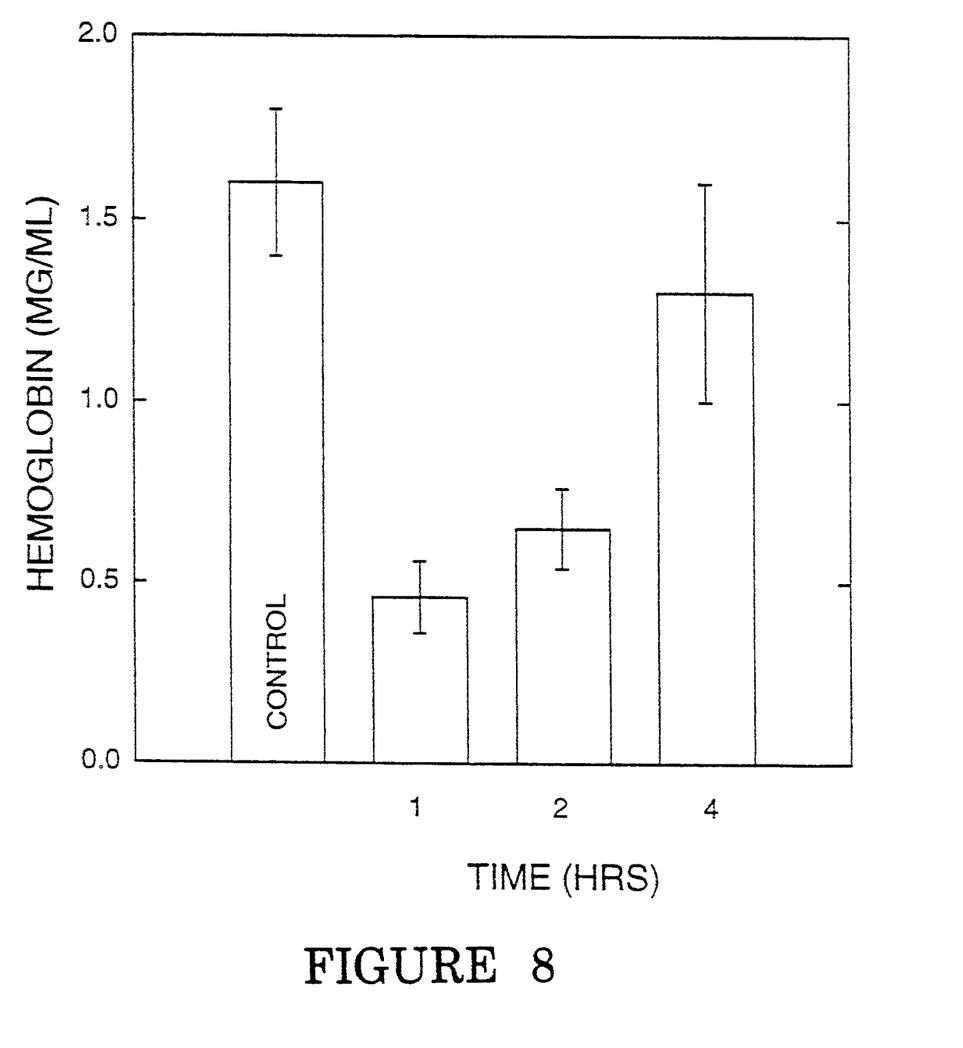

MDL-101,028 was administered to rats at various time intervals before instillation of elastase to determine the duration of action. Administration of elastase intratracheally to rats resulted in hemorrhagic lung fluid that contained 1.5±0.2 (mean±S.E.M., n=20) mg/ml of hemoglobin (FIG. 8). Administration of MDL-101,028 1, 2, or 4 hours before elastase resulted in the inhibition of lung hemorrhage of 61%, 63%, and 20% respectively (FIG. 8). Therefore, the duration of action by the intratracheal route was greater than two hours and less than four hours.

The compounds of the present invention may be administered by a variety of routes. The compounds may also be administered orally or parenterally (i.e. subcutaneously, intravenously, intramuscularly, intraperitoneally, or intratracheally). More specifically, the present invention provides a method for the treatment of a patient afflicted with pulmonary diseases including adult respiratory distress syndrome (ARDS), chronic bronchitis, cystic fibrosis, emphysema and inflammatory diseases of joint tissues such as arthritis, wherein such disease states may be treated by the administration of an effective inhibitory amount of a compound of the present invention to a patient in need thereof.

A therapeutically effective inhibitory amount of a compound of the present invention refers to an amount which is effective in controlling connective tissue degradation that may be associated with adult respiratory distress syndrome, cystic fibrosis, acute bronchitis, emphysema and arthritis. The term "controlling" is intended to refer to all processes wherein there may be a slowing, interrupting, arresting, or stopping of the progression of the disease and does not necessarily indicate a total elimination of all disease symptoms.

A therapeutically effective inhibitory amount of the compounds used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

A therapeutically effective amount of a compound of formula (1) is expected to vary from about 0.1 milligram per kilogram of body weight per day (mg/kg/day) to about 100 mg/kg/day. Preferred amounts are able to be determined by one skilled in the art. One skilled in the art of preparing formulations can readily select the proper form and mode of administration depending upon the particular characteristics of the compound selected the disease state to be treated, the stage of the disease, and other relevant circumstances (Remington's Pharmaceutical Sciences, 18th Edition, Mack Publishing Co. (1990)).

Pharmaceutical compositions can be manufactured utilizing techniques known in the art. Typically a protective amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of this invention can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations-are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

As used herein, the term "patient" refers to a warm blooded animal such as a mammal which is afflicted with a particular inflammatory disease state. It is understood that guinea pigs, dogs, cats, rats, mice, horses, cattle, sheep, and humans are examples of animals within the scope of the meaning of the term.

What is claimed is:

1. A method of controlling connective tissue degradation by administering to a patient in need thereof a therapeutically effective amount of a compound of the formula:

wherein n is a whole number within the range of 5 to 10 inclusive and the pharmaceutically acceptable salts thereof.

2. A method of controlling connective tissue degradation of claim 1 with said compound wherein n is 6.

3. A method of one of claims 1-2 for controlling connective tissue degradation occurring in adult respiratory distress syndrome.

4. A method of one of claims 1-2 for controlling connective tissue degradation occurring in cystic fibrosis.

5. A method of one of claims 1-2 for controlling connective tissue degradation occurring in acute bronchitis.

6. A method of one of claims 1-2 for controlling connective tissue degradation occurring in emphysema.

7. A method of one of claims 1-2 for controlling connective tissue degradation occurring in arthritis.

8. A method of one of claims 1-2 for controlling connective tissue damage by inhibiting the damage induced by neutrophils.

9. A method of one of claims 1-2 for controlling connective tissue damage by inhibiting the damage induced by elastase.

10. A method of one of claims 1-2 for controlling connective tissue damage by inhibiting the damage induced by cathepsin G.

11. A method of one of claims 1-2 for controlling connective tissue degradation using said compounds with pharmaceutically acceptable carrier.

* * * * *

UNITED STATES PATENT AND TRADEMARK OFFICE
CERTIFICATE OF CORRECTION

PATENT NO. : 5,384,119
DATED : January 24, 1995
INVENTOR(S) : Michael J. Janusz

It is certified that error appears in the above-indentified patent and that said Letters Patent is hereby corrected as shown below:

Column 1, line 64 the patent reads "Goldstein & Doting" and should read -- Goldstein & Doring--.

Column 1, line 68 the patent reads "1989." and should read --1989;--.

Column 2, line 14 the patent reads "652-689" and should read --682-689--.

Column 5, line 31 the patent reads "Catheosin" and should read --Cathepsin--.

Signed and Sealed this

Twenty-sixth Day of March, 1996

Attest:

BRUCE LEHMAN

*Attesting Officer*      *Commissioner of Patents and Trademarks*